United States Patent [19]

Inamasa et al.

[11] Patent Number: 5,321,178
[45] Date of Patent: Jun. 14, 1994

[54] PROCESS FOR PRODUCING 2,6-DIMETHYLNAPHTHALENE

[75] Inventors: Kenji Inamasa; Norio Fushimi; Makoto Takagawa, all of Tsukuba, Japan

[73] Assignee: Mitsubishi Gas Chemical Company, Inc., Tokyo, Japan

[21] Appl. No.: 6,807

[22] Filed: Jan. 21, 1993

[30] Foreign Application Priority Data

Feb. 26, 1992 [JP] Japan .................................. 4-039536

[51] Int. Cl.$^5$ ............................................... C07C 5/00
[52] U.S. Cl. .................................. 585/411; 585/407; 585/419; 585/420
[58] Field of Search ............... 585/411, 407, 709, 418, 585/419

[56] References Cited

U.S. PATENT DOCUMENTS

| | | | |
|---|---|---|---|
| 3,931,348 | 1/1976 | Taniguchi et al. | 585/411 |
| 4,650,565 | 3/1987 | Jacobson et al. | 208/138 |
| 5,068,480 | 11/1991 | Takagawa et al. | 585/411 |
| 5,185,484 | 2/1993 | Del Rossi et al. | 585/419 |

Primary Examiner—Asok Pal
Assistant Examiner—P. Achutamurthy
Attorney, Agent, or Firm—Frishauf, Holtz, Goodman & Woodward

[57] ABSTRACT

A process for efficiently producing 2,6-dimethylnaphthalene which comprises subjecting 2-methyl-1-(p-tolyl)butene and/or 2-methyl-1-(p-tolyl)butane as the starting raw material to a cyclization dehydrogenation reaction in the presence of a catalyst comprising (a) a palladium component, (b) an alkali or alkaline earth metal compound and (c) aluminum oxide. The process enables the production of highly pure 2,6-dimethylnaphthalene in a high yield at a low cost. The catalyst used in the process affords high safety and stability.

19 Claims, No Drawings

PROCESS FOR PRODUCING 2,6-DIMETHYLNAPHTHALENE

BACKGROUND OF THE INVENTION

1. Field of the Invention

The present invention relates to a process for producing 2,6-dimethylnaphthalene. More particularly, it pertains to a catalyst for producing 2,6-dimethylnaphthalene which is useful as a starting raw material for 2,6-naphthalene dicarboxylic acid.

2,6-Napthalene dicarboxylic acid has an industrially important use as a starting raw material for high-performance polyester, polyethylene naphthalate fibers and films having excellent tensile strength and heat resistance.

2. Description of Related Art 2,6-Dimethylnaphthalene has heretofore been obtained by isolating it from a coal tar fraction or a fraction of heavy oil subjected to fluid catalytic cracking (FCC). However, the aforementioned isolation process affords the fraction in the form of a mixture containing almost all the types of methyl group-position isomers such as 1,2-, 1,3-, 1,4-, 1,5-, 1,6-, 1,7-, 1,8-, 2,3- and 2,7-dimethylnaphthalene in addition to the objective 2,6-dimethylnaphthalene. Thus, the process for isolating and purifying 2,6-dimethylnaphthalene from such fraction mixture suffers from the disadvantage of a number of steps and a high cost required in the production thereof, making itself unsuitable for inexpensive mass-production of 2,6-dimethylnaphthalene.

There have recently been proposed several processes for producing 2,6-dimethylnaphthalene from a variety of starting raw materials, but there has not yet been established an industrial production process capable of efficiently and selectively synthesizing 2,6-dimethylnaphthalene by the use of inexpensive starting raw material available in a large quantity.

Examples of the above-mentioned process include the process disclosed in Japanese Patent Application Laid-Open Nos. 172937/1985, 29536/1987 and 8344/1988 in which naphthalene or monomethylnaphthalene is methylated into dimethylnaphthalene and the process disclosed in Japanese Patent Application Laid-Open Nos. 45536/1985 and 14737/1988 in which naphthalene or monomethylnaphthalene is transmethylated into dimethylnaphthalene by using polymethylbenzene.

Nevertheless, the process disclosed in any of the aforesaid laid-open patent applications suffers from the defects that the conversion of naphthalene and monomethylnaphthalene to 2,6-dimethylnaphthalene is low and selective production of 2,6-dimethylnaphthalene is difficult. Consequently, the process necessitates complicated isolating purification steps and intricate isomerization steps, thus causing disadvantageous problems from the industrial point of view.

In addition, Japanese Patent Application Laid-Open Nos. 61647/1973 and 48647/1974 disclose a process for production of 2,6-dimethylnaphthalene by cyclization, dehydrogenation and isomerization of 5-(o-tolyl)pentene-2 to be used as a starting material. Moreover, Japanese Patent Publication Nos. 17983/1975, 17985/1975 and 22550/1975 disclose a process for producing dimethylnaphthalene by the cyclization dehydrogenation of 5-(o-tolyl)pentene-2.

In the above-mentioned processes, however, 5-(o-tolyl)pentene-2 to be used as a starting material is usually produced from o-xylene and 1,3-butadiene by the use of an alkali metal such as potassium or sodium as a catalyst, and many problems remain unsolved with, regard to the catalyst handling, especially with respect of safety. Likewise, as the resultant dimethylnaphthalene is obtained as the mixture of isomers such as 1,5-dimethylnaphthalene, 1,6-dimethylnaphthalene, 2,6-dimethylnaphthalene and the like, the production of 2,6-dimethylnaphthalene therefrom suffers a lot of disadvantages that the steps of isomerization, separation and purification are necessary.

On the other hand, attempts have been made to selectively produce 2,6-dimethylnaphthalene by cyclization and dehydrogenation of 2-methyl-1-(p-tolyl)butene or 2-methyl-1-(p-tolyl)butane as disclosed, for example, in Japanese Patent Publication No. 5292/1978 wherein a catalyst comprising rhenium oxide, an alkali metal oxide or alkaline earth metal oxide and alumina is used, and in Japanese Patent Publication No. 1701/1976 wherein a catalyst of chromia/alumina series containing an alkali metal oxide is employed.

However, the above-disclosed catalysts are unfavorable, since the use thereof results in a low yield and an insufficient purity of the objective 2,6-dimethylnaphthalene; besides the highly toxic chromium compound contained therein will bring about environmental pollution problems.

It has been disclosed by the present inventors, in Japanese Patent Application Laid-Open Nos. 173834/1991 and 251545/1991, that in the production of 2,6-dimethylnaphthalene by cyclization dehydrogenation of 2-methyl-1-(p-tolyl)butene or 2-methyl-1-(p-tolyl)butane, 2,6-dimethylnaphthalene with high purity is obtained at a relatively high yield by the application of a catalyst comprising lead and alumina incorporated with a third component and a catalyst comprising indium and alumina incorporated with a third component. Nevertheless, the above-developed catalysts still involve some problems such that the catalyst containing a lead component is industrially unfavorable due to its toxicity and the catalyst containing an indium component sometimes evaporates away during its use owing to the high volatility of a monovalent indium compound formed during the reaction and the like. Under such circumstances, it has been sought for a long time to develop a catalyst capable of producing highly pure 2,6-dimethylnaphthalene at a high yield with a stabilized operation without causing any problem relating to sanitation.

In the case where 2-methyl-1-(p-tolyl)butene or 2-methyl-1-(p-tolyl)-butane as a raw material is reacted by the use of a catalyst consisting of aluminum oxide alone, dimethylnaphthalene is generally produced but the yield thereof is too low and unfavorable side reaction such as isomerization, decomposition and polymerization of a raw material are too excessive to make the catalyst industrially usable.

The application of a catalyst consisting of aluminum oxide incorporated with a palladium component to the above reaction improves the selectivity to cyclization dehydrogenation and increases the yield of dimethylnaphthalene, but remarkable side reactions such as isomerization and demethylation of the resultant dimethylnaphthalene takes place together with decomposition and polymerization of a raw material, thus unfavorably lowering the selectivity to the objective 2,6-dimethylnaphthalene.

On the other hand, the application of a catalyst consisting of an alkali metal component or an alkaline earth metal component each supported on aluminum oxide can suppress decomposition and polymerization of 2-methyl-1-(p-tolyl)butene or 2-methyl-1-(p-tolyl)butane as a raw material, but the catalyst scarcely exhibits cyclization dehydrogenation activity or even if it exhibits the activity, the yield of dimethylnaphthalene is too low to make the catalyst industrially usable.

Specifically, the use of a catalyst consisting only of aluminum oxide unfavorably causes a variety of side reactions due to acid points on the surface of the catalyst including isomerization, decomposition and polymerization of a raw material to take place in the reaction process.

In view of the above, intensive research and investigation were concentrated by the present inventors in order to solve and overcome the above-mentioned problems. As a result, it has been discovered by the present inventors that highly pure 2,6-dimethylnaphthalene is obtained at a high yield by the use of a catalyst comprising a palladium component, at least one compound selected from alkali metal compounds and alkaline earth metal compounds and aluminum oxide. The present invention has been accomplished on the basis of the above-mentioned finding and information.

SUMMARY OF THE INVENTION

It is the general object of the present invention to provide a process for efficiently producing 2,6-dimethylnaphthalene.

It is another object of the present invention to provide a process for producing highly pure 2,6-dimethylnaphthalene at a high yield and at a low cost from inexpensive and readily available starting raw materials by the use of a catalyst with enhanced safety and stability.

It is still another object of the present invention to provide a catalyst for use in the process for efficiently producing 2,6-dimethylnaphthalene by cyclization dehydrogenation of a starting raw material.

Other objects of the present invention will be obvious from the description of this text hereinafter disclosed.

Specifically, the present invention provides a process for producing 2,6-dimethylnaphthalene which comprises subjecting 2-methyl-1-(p-tolyl)butene, 2-methyl-1-(p-tolyl)butane or mixture thereof as a starting raw material to a cyclization dehydrogenation reaction by the use of a catalyst comprising a (a) palladium component, (b) at least one compound selected from alkali metal compounds and alkaline earth metal compounds, and (c) aluminum oxide.

DESCRIPTION OF PREFERRED EMBODIMENT

As described herein before, the catalyst to be employed in the present invention comprises a (a) palladium component; (b) an alkali metal compound or an alkaline earth metal compound; and (c) aluminum oxide. By mitigating the unreasonably strong acid points on the aluminum oxide with (b) an alkali metal compound or an alkaline earth metal compound and at the same time, incorporating a (a) palladium component having intense dehydrogenation capability in the catalyst, the catalyst according to the present invention can drastically improve the reaction selectivity directed to 2,6-dimethylnaphthalene in a cyclization dehydrogenation reaction of 2-methyl-1-(p-tolyl)butene or 2-methyl-1-(p-tolyl)butane.

In the catalyst according to the present invention, the amount of the palladium component supported on aluminum oxide is 0.05 to 20%, preferably 0.1 to 10% by weight expressed in terms of metallic palladium based on the amount of aluminum oxide. An amount of the palladium less than 0.05% by weight sometimes results in insufficient dehydrogenation capability and low conversion efficiency of a raw material such as 2-methyl-1-(p-tolyl)butene or 2-methyl-1-(p-tolyl)butane, whereas that exceeding 20% by weight leads to a large usage of expensive metallic palladium, making the catalyst rather impractical.

The type or kind of the alkali metal compound or the alkaline earth metal compound to be added to the catalyst according to the present invention is not specifically limited but is enumerated by lithium nitrate, sodium nitrate, potassium nitrate, lithium chloride, sodium chloride, potassium chloride, calcium oxide, calcium hydroxide and the like.

In addition, in the catalyst according to the present invention, the amount of the alkali metal compound or alkaline earth metal compound is usually 0.1 to 20%, preferably 1 to 10% by weight expressed in terms of alkali or alkaline earth metal based on the amount of aluminum oxide. An amount of the alkali or alkaline earth metal less than 0.1% by weight leads to insufficient mitigation of acid points on alumina (aluminum oxide), thus causing remarkable isomerization, decomposition, polymerization or the like of 2-methyl-1-(p-tolyl)butene or 2-methyl-1-(p-tolyl)butane as a raw material, while that exceeding 20% by weight is unfavorable, since it fails to embody the catalytic activity and suppresses a cyclization dehydrogenation reaction.

The process for producing the catalyst of the present invention comprising (a) palladium, (b) an alkali or alkaline earth metal compound (c) aluminum oxide (alumina) is not specifically limited, but may be in accordance with one of a variety of previously known processes.

Examples of the process for producing the catalyst of the present invention include the process in which (c) alumina is impregnated simultaneously with (a) a palladium compound and (b) an alkali or alkaline earth metal compound to be supported thereon; the process in which (c) aluminum oxide is impregnated once with a (a) palladium compound followed by impregnating the (c) aluminum oxide with (b) an alkali or alkaline earth metal compound; and conversely the process in which the mixture of (b) an alkali or alkaline earth metal compound and (c) aluminum oxide is impregnated with (a) a palladium compound.

In the case of impregnating (c) aluminum oxide with (a) a palladium compound, there are preferably employed as the palladium source a solution of palladium chloride, palladium nitrate, palladium acetate, chloropalladic acid, palladium sodium chloride, palladium potassium chloride, tetraaminepalladium (II) complex, etc. in water or a suitable organic solvent such as methanol and acetone.

There are available a variety of methods and conditions for supporting (a) a palladium or compound thereof on (c) aluminum oxide, of which is preferable the method wherein the palladium or compound thereof is uniformly dispersed in (c) aluminum oxide while being adjusted in the amount to be supported thereon.

There is no specific limitation to the method for adding an (b) alkali or alkaline earth metal compound to (c)

aluminum oxide in preparing the catalyst of the present invention insofar as the compound is uniformly dispersed on the (c) aluminum oxide. There are available, for example, the method in which (c) aluminum oxide is impregnated with a solution of a salt of such metal; the method in which aluminum oxide is kneaded with the above solution; the method in which the above solution is simultaneously added to the production process of aluminum oxide; and like methods.

The ordinary process for preparing the catalyst of the present invention comprises, as described hereinbefore, immersion-impregnating aluminum oxide with a palladium component, followed by drying and calcining to obtain at first the palladium component supported on alumina and then adding the aforestated alkali or alkaline earth metal compound.

There is also adaptable the process wherein a palladium component and an alkali or alkaline earth metal compound are supported on alumina at the same time.

The catalyst precursor mixture thus prepared is subjected to necessary treatment such as drying, calcining, molding and reduction to be made into the catalyst for use in the present invention. Drying is carried out usually at room temperature or higher, preferably at 70° to 130° C. and calcining, when necessary, is effected preferably at 300° to 800° C. In the case of molding, tableting, extrusion or the like is adopted. In the case of reduction, there is preferably adopted. In the case of reduction, there is preferably adopted a method in which hydrogenation treatment is carried out at 300° to 700° C. or a method in which is used a reducing agent such as sodium borohydride, hydrazine or the like.

2-Methyl-1-(p-tolyl)butene to be subjected to cyclication dehydrogenation reaction in the present invention can contain the following six (6) isomers due to double bond position and geometry including cis and trans forms.

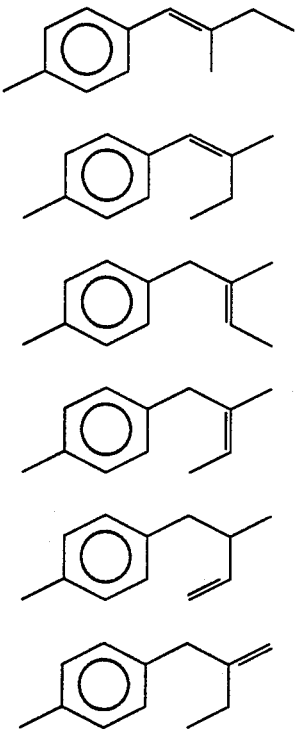

Any of the above-illustrated isomers alone or in the form of mixture with at least one other isomer may be put into application without any problem.

There is proposed a process for industrial production of 2-methyl-1-(p-tolyl)butene from the raw materials for general purpose as follows:

For example, U.S. Pat. No. 5,008,479 discloses a process for producing 2-methyl-1-(p-tolyl)butene which comprises the steps of (1) acylation step in which toluene, butene and carbon monoxide are synthesized into 2,4-dimethyl-isobutyrophenone; (2) hydrogenation step in which the resultant 2,4-dimethylisobutyrophenone is hydrogenated into p-tolyl-sec-butyl carbinol; and (3) dehydration step in which the resultant p-tolyl-sec-butyl carbinol is dehydrated into 2-methyl-1-(p-tolyl)-butene. In the above-mentioned process, the objective 2-methyl-1-(p-tolyl)butene obtained through the dehydration step comprises as principal ingredients the isomers [1] and [2] among the above-illustrated six isomers but can be made into a mixture comprising all types of the aforestated isomers by appropriately selecting the type of catalyst or reaction conditions in the above dehydration step.

According to the above-described process, the objective 2-methyl-1-(p-tolyl)butene can be produced in a high selectivity at a low cost from widely available starting raw materials. In addition to the above-described process, various processes may be employed.

Examples of the process for producing the publicly known 2-methyl-1-(p-tolyl)butane include the process wherein butene is addition-reacted with p-xylene in the presence of an alkali metal catalyst (refer to Japanese Patent Application Laid-Open Nos. 93952/1975 and 209027/1987), the process wherein 2,4-dimethylisobutyrophenone is subjected to hydrogenation dehydration as disclosed in the above U.S. Pat. No. 5,008,479 and various different processes.

The present invention pertains to the process for producing 2,6-dimethylnaphthalene by the cyclization dehydrogenation reaction of 2-methyl-1-(p-tolyl)butene and/or 2-methyl-1-(p-tolyl)butane using the above-described catalyst. In the above-mentioned reaction, the reaction pressure may be lower than, equal to or higher than atmospheric pressure but is preferably in the range of atmospheric pressure to 2 kg/cm² with the reaction temperature of 350° to 700° C., preferably 450° to 650° C.

In the case where 2-methyl-1-(p-tolyl)butane is used as a raw material, it is desirable to raise the reaction temperature or decrease the SV (space velocity) in order to compensate for the reactivity of the above material somewhat lower than that of 2-methyl-1-(p-tolyl)butene in the cyclization dehydrogenation. The objective 2,6-dimethylnaphthalene is in the form of solid with a melting point of 112° C. and preferably produced from 2-methyl-1-(p-tolyl)butene or 2-methyl-1-(p-tolyl)butane as the starting raw material by dissolving or diluting the material in or with toluene, benzene, steam or the like in view of the reaction procedure and also the purpose of suppressing side reaction such as polymerization.

According to the present invention, isomerization into the isomers other than 2,6-dimethylnaphthalene is suppressed; selectivity to and yield of 2,6-dimethylnaphtalene is drastically improved; and besides an industrially secured and stabilized operation can be assured which is free from a toxic component or the component vaporized away during the reaction.

In the following the present invention will be specifically described with reference to examples and comparative examples, but it shall not be limited thereto.

EXAMPLE 1

An aqueous acidic solution of 1.67 g of palladium chloride in hydrochloric acid was added to 100 g of alumina under stirring at 50° C. for 2 hours to carry out impregnation. The water in the mixture was distilled away at 70° C. under reduced pressure and then the residual mixture was dried overnight at 115° C. and calcined at 550° C. in the air to prepare a preparatory catalyst of palladium component supported on alumina. The preparatory catalyst was added to an aqueous solution of 29.8 g of lithium nitrate with stirring at 50° C. for 2 hour to effect further impregnation. The resultant mixture was dried at 70° C. under reduced pressure and then at 115° C. overnight, followed by calcining at 550° C. in the air.

Subsequently 10 g of the above palladium-lithium-alumina catalyst was packed in a tubular reactor made of quartz glass with 12 mm inside diameter and 300 mm length, reduced at 550° C. for 5 hours in a stream of hydrogen and maintained at 520° C. Then 2-methyl-1-(p-tolyl)butene mixture [62% 2-methyl-1-(p-tolyl)-1-butene, 26% 2-methyl-1-(p-tolyl)-2-butene and 12% other isomers] was dissolved in toluene to prepare 10% by weight of solution which was vaporized at 10 g/hour through a preheating layer, and the resultant vapor was fed to the catalyst layer together with $N_2$ gas of 50 ml/min to carry out cyclization dehydrogenation reaction at atmospheric pressure. The reaction product in the form of liquid was analyzed for conversion efficiency of 2-methl-1-(p-toyly)butene mixture and selectivity to 2,6-dimethylnaphthalene. The results are given in Table 1.

EXAMPLE 2

An aqueous solution of 2.76 g of palladium sodium chloride ($Na_2PdCl_4$) and 9.49 g of sodium nitrate was added to 100 g of alumina under stirring at 50° C. for 2 hours to carry out impregnation. The water in the mixture was distilled away 70° C. under reduced pressure and then the residual mixture was dried overnight at 115° C. and calcined at 550° C. in the air to prepare a catalyst of palladium component supported on alumina.

Subsequently 10 g of the above palladium-sodium-alumina catalyst was packed in a tubular reactor made of quartz glass with 12 mm inside diameter and 300 mm length, reduced at 550° C. for 5 hours in a stream of hydrogen and maintained at 520° C. Then 2-methyl-1-(p-toly)-2-butene mixture [48% 2-methyl-1-(p-tolyl)-butene, 41% 2-methyl-1-(p-tolyl)-2-butene and 11% other isomers] was dissolved in toluene to prepare 10% by weight of solution, which was vaporized at 10 g/hour through a preheating layer, and the resultant vapor was fed to the catalyst layer together with $N_2$ gas of 50 ml/min t carry out cyclization dehydrogenation reaction at atmospheric pressure.

The reaction results are given in Table 1.

EXAMPLE 3

The procedure in Example 2 was repeated to carry out a cyclization dehydrogenation reaction except that distilled water was fed to the catalyst layer at one (1) g/hour via the preheating layer in addition to 2-methyl-1-(p-tolyl)butene mixture at 10 g/hour. The reaction results are given in Table 1.

EXAMPLE 4

Palladium chloride in an amount of 1.67 g was dissolved in hydrochloric acid and the solution was vaporized to bone dryness to prepare chloropalladic acid ($H_2PdCl_4$), which was again dissolved in water. The resultant solution was added to 100 g of alumina that had been incorporated with 7.76 g of potassium nitrate to impregnate thereinto under stirring at 70° C. for 2 hours. The water in the mixture was distilled away at 70° C. under reduced pressure and the residual mixture was dried overnight at 115° C. and calcined at 550° C. in the air to prepare a catalyst. By the use of the catalyst thus prepared comprising one (1) % palladium and 3% potassium each supported on alumina, the reaction was carried out in the same manner as in Example 1. The reaction results are given in Table 1.

EXAMPLE 5

The procedure in Example 4 was repeated to carry out a cyclization dehydration reaction except that distilled water was fed to the catalyst layer at one (1) g/hour via the preheating layer in addition to 2-methyl-1-(p-tolyl)butene mixture at 10 g/hour. The reaction results are given in Table 1.

COMPARATIVE EXAMPLE 1

The procedure in Example 1 was repeated to carry out a cyclization dehydration reaction except that the preparatory catalyst comprising 1% by weight of palladium component supported on alumina obtained in Example 1 was used as such without the impregnation of the alkali metal. The reaction results are given in Table 1.

COMPARATIVE EXAMPLE 2

Lithium nitrate in an amount of 29.8 g was dissolved in deionized water, and to the resultant solution was added 100 g of alumina under stirring at 50° C. for 2 hours to effect impregnation. The resultant mixture was dried at 70° C. under reduced pressure and then at 115° C. overnight, followed by being calcined at 550° C. in the air.

Subsequently 10 g of the above lithium-alumina catalyst was packed in a tubular reactor made of quartz glass with 12 mm inside diameter and 300 mm length and maintained at 520° C. Then, a solution of 10% by weight of 2-methyl-1-(p-tolyl)butene mixture in toluene same as that used in Example 1 was vaporized at 10 g/hour through a preheating layer, and the resultant vapor was fed to the catalyst layer together with $N_2$ gas of 50 ml/min to carry out cyclization dehydrogenation reaction at atmospheric pressure. The reaction results are given in Table 1.

COMPARATIVE EXAMPLE 3

The procedure in Comparative Example 2 was repeated to carry out a cyclization dehydrogenation reaction except that 7.76 g of potassium nitrate was used in place of lithium nitrate to prepare a catalyst. The reaction results are given in Table 1.

EXAMPLE 6

The procedure in Example 1 was repeated to prepare a catalyst and carry out a cyclization dehydrogenation reaction except that 0.83 g of palladium chloride and 12.9 g of potassium nitrate instead of lithium nitrate were used. The results are given in Table 1.

EXAMPLE 7

The procedure in Example 6 was repeated to carry out a cyclization dehydration reaction except that 5.00 g of palladium chloride and 7.76 g of potassium nitrate were used. The reaction results are given in Table 1.

EXAMPLE 8

Tetraaminepalladium (II) nitrate [(NH$_3$)$_4$Pd(NO$_3$)$_2$] in an amount of 0.84 g and 2.33 g of potassium nitrate were dissolved in 50 mL of deionized water, and the resultant solution was added to 30 g of alumina under stirring at 50° C. for 2 hours to effect impregnation. The water in the mixture was distilled away at 70° C. under reduced pressure and the residual mixture was dried overnight at 115° C. and calcined at 550° C. in the air to prepare a catalyst.

By the use of the catalyst thus prepared comprising the above-mentioned pallaidum-potassium-alumina, the cyclization dehydration reaction was carried out in the same manner as Example 1. The reaction results are given in Table 1.

EXAMPLE 9

An aqueous acidic solution of 0.83 g of palladium chloride in hydrochloric acid was incorporated with 50 g of oxide complex consisting of calcium oxide and aluminum oxide (atomic ratio of 1:4) under stirring at 50° C. for 2 hours to carry out impregnation. The water in the mixture was distilled away at 70° C., under reduced pressure. Subsequently, 10 g of the above palladium-calcium alumina catalyst was packed in a tubular reactor made of quartz glass with 12 mm inside diameter and 300 mm length, reduced at 550° C. for 5 hours in a stream of hydrogen and maintained at 520° C. Then 2-methyl-1-(p-tolyl)butene mixture 62% 2-methyl-1-(p-tolyl)-1-butene, 26% 2-methyl-1-(p-tolyl)-2-butene and 12% other isomers was dissolved in toluene to prepare 10% by weight of solution, which was vaporized at 10 g/hour through a preheating layer, and the resultant vapor was fed to the catalyst layer together with N$_2$ gas of 50 ml/min to carry out a cyclization dehydrogenation reaction at atmospheric pressure. The reaction results are given in Table 1.

EXAMPLE 10

The catalyst as used in Example 7 was pretreated similarly to Example 7 and the reaction temperature was maintained at 530° C. Separately, 2-methyl-1-(p-tolyl)butane was dissolved in benzene to prepare a solution containing the same by 5% by weight, which was vaporized at 10 g/hour through a preheating layer, and the resultant vapor was fed to the catalyst layer together with N$_2$ gas of 50 ml/min to carry out a cyclization dehydrogenation reaction at atmospheric pressure. The reaction results are given in Table 1.

As a result, the objective 2,6-dimethylnaphthalene was obtained at a conversion efficiency of 2-methyl-1-(p-tolyl)butane of 79.3% and a selectivity to 2,6-dimethylnaphthalene of 66.7%.

TABLE 1

| No. | Catalyst (*) | Palladium source | Alkali source** | Temperature (°C.) | Water | Conversion efficiency (%) | Selectivity to 2,6-DMN (%) |
|---|---|---|---|---|---|---|---|
| Example 1 | Pd(1)-Li(3) | PdCl$_2$ | LiNO$_3$ | 520 | absent | 95.0 | 72.3 |
| Example 2 | Pd(1)-Na(3) | Na$_2$PdCl$_4$ | NaNO$_3$ | 520 | absent | 96.5 | 71.8 |
| Example 3 | Pd(1)-Na(3) | Na$_2$PdCl$_4$ | NaNO$_3$ | 530 | present | 95.3 | 72.5 |
| Example 4 | Pd(1)-K(3) | H$_2$PdCl$_4$ | KNO$_3$ | 520 | absent | 94.0 | 74.1 |
| Example 5 | Pd(1)-K(3) | H$_2$PdCl$_4$ | KNO$_3$ | 530 | present | 94.5 | 73.4 |
| Comparative Example 1 | Pd(1) | PdCl$_2$ | — | 490 | absent | 99.2 | 23.5 |
| Comparative Example 2 | Li(2) | — | LiNO$_3$ | 520 | absent | 33.3 | 26.8 |
| Comparative Example 3 | K(3) | — | KNO$_3$ | 520 | absent | 77.0 | 61.3 |
| Example 6 | Pd(0.5)-K(5) | PdCl$_2$ | KNO$_3$ | 520 | present | 93.1 | 72.8 |
| Example 7 | Pd(3)-K(3) | PdCl$_2$ | KNO$_3$ | 520 | absent | 96.3 | 73.5 |
| Example 8 | Pd(1)-K(3) | (NH$_3$)$_4$Pd(NO$_3$)$_2$ | KNO$_3$ | 520 | absent | 95.2 | 71.3 |
| Example 9 | Pd(1) | PdCl$_2$ | CaO | 520 | absent | 93.7 | 69.8 |

[Remarks]
(*): Figures in parenthesis indicate % by weight based on alumina weight.
**More specifically, it represents an alkali metal source or an alkaline earth metal source.

What is claimed is:

1. A process for producing 2,6-dimethylnaphthalene which comprises subjected 2-methyl-1-(p-tolyl)butene, 2-methyl-1-(p-tolyl)butane or a mixture thereof as a starting raw material to a cyclization dehydrogenation reaction in the presence of a catalyst comprising (a) a palladium component, (b) at least one compound selected from the group consisting of alkali metal compounds and alkaline earth metal compounds and (c) aluminum oxide.

2. The process according to claim 1 wherein the amount of the (a) palladium component supported on (c) aluminum oxide is 0.05 to 20% by weight expressed in terms of metallic palladium based on the aluminum oxide.

3. The process according to claim 1 wherein the amount of the (b) at least one compound selected from the group consisting of alkali metal compounds and alkaline earth metal compounds is 0.1 to 20% by weight based on the (c) aluminum oxide.

4. The process according to claim 1 wherein said catalyst comprises (a) a palladium component, (b) a alkali metal compound and (c) aluminum oxide.

5. The process according to claim 1 wherein said catalyst comprises (a) a palladium component, (b) a alkaline earth metal compound and (c) aluminum oxide.

6. The process according to claim 2 wherein said alkali metal is selected from the group consisting of sodium, potassium, lithium and cesium.

7. The process according to claim 3 wherein said alkaline earth metal is selected from the group consisting of beryllium, magnesium, calcium and strontium.

8. The process according to claim 1 wherein the cyclization dehydrogenation reaction is carried out at a temperature of 300° to 700° C. and a pressure of atmospheric pressure to 2 kg/cm².

9. The process according to claim 1 wherein the (b) alkali metal compound is selected from the group consisting of lithium chloride, lithium nitrate, sodium chloride, sodium nitrate, potassium chloride and potassium nitrate.

10. The process according to claim 1 wherein the (a) palladium component is selected from the group consisting of palladium chloride, palladium nitrate, palladium acetate, chloropalladic acid, palladium sodium chloride, palladium potassium chloride and tetraaminepalladium salt.

11. The process according to claim 1 wherein the amount of the palladium component (a) supported on the aluminum oxide (c) is 0.1 to 10% by weight expressed in terms of metallic palladium based on the aluminum oxide.

12. The process according to claim 11 wherein the amount of the at least one compound selected from the group consisting of alkali metal compounds and alkaline earth metal compounds (b) is 1 to 10% by weight based on the aluminum oxide (c).

13. The process according to claim 12 wherein the reaction is carried out at a temperature of 450° to 650° C. and at a pressure of atmospheric pressure to 2 kg/cm².

14. The process according to claim 13 wherein the palladium component (a) is selected from the group consisting of palladium chloride, palladium nitrate, palladium acetate, chloropalladic acid, palladium sodium chloride, palladium potassium chloride and tetraaminepalladium salt.

15. The process according to claim 14 wherein said (b) is an alkali metal compound selected from the group consisting of lithium chloride, lithium nitrate, sodium chloride, sodium nitrate, potassium chloride, potassium nitrate.

16. The process according to claim 14 wherein said (b) is an alkaline earth metal compound selected from the group consisting of beryllium, magnesium, calcium and strontium.

17. The process according to claim 14 wherein the starting raw material is 2-methyl-1-(p-tolyl)butene.

18. The process according to claim 14 wherein the starting raw material is 2-methyl-1-(p-tolyl)butane.

19. The process according to claim 14 wherein the starting material is a mixture of 2-methyl-1-(p-tolyl)butene and 2-methyl-1-(p-tolyl)butane.

* * * * *